United States Patent
Munk et al.

(10) Patent No.: US 6,726,661 B2
(45) Date of Patent: Apr. 27, 2004

(54) AIR SHOT MECHANISM FOR ELECTRONIC INJECTION DEVICES

(75) Inventors: Jens Munk, Olstykke (DK); Denmark Denmark Aasmul, Holte (DK); Henrik Ljunggreen, Ballerup (DK); Lars Hofmann Christensen, Jylinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/315,871

(22) Filed: Dec. 10, 2002

(65) Prior Publication Data

US 2003/0083626 A1 May 1, 2003

Related U.S. Application Data

(63) Continuation of application No. 09/672,662, filed on Sep. 28, 2000, now Pat. No. 6,514,230.
(60) Provisional application No. 60/160,130, filed on Oct. 18, 1999, and provisional application No. 60/170,017, filed on Dec. 10, 1999.

(30) Foreign Application Priority Data

Oct. 12, 1999 (DK) .......................................... 1999 01451
Dec. 3, 1999 (DK) .......................................... 1999 01732

(51) Int. Cl.[7] .......................... A61M 5/00; A61M 37/00; A61M 5/178
(52) U.S. Cl. ....................... 604/207; 604/208; 604/154; 604/186; 604/187; 604/191
(58) Field of Search ............................. 604/207, 208, 604/154, 186, 187, 191

(56) References Cited

U.S. PATENT DOCUMENTS

| | | | | |
|---|---|---|---|---|
| 5,947,934 A | * | 9/1999 | Hansen et al. | 604/207 |
| 6,110,149 A | * | 8/2000 | Klitgaard et al. | 604/209 |
| 6,340,357 B1 | * | 1/2002 | Poulsen et al. | 604/208 |
| 6,514,230 B1 | * | 2/2003 | Munk et al. | 604/207 |

* cited by examiner

Primary Examiner—William C. Doerrler
Assistant Examiner—Filip Zec
(74) Attorney, Agent, or Firm—Reza Green, Esq.; Richard W. Bork, Esq.; Marc A. Began, Esq.

(57) ABSTRACT

Described is an electronic injection device wherein an electronic circuit is designed to work in two alternative modes: an air shot mode and a dose injection mode. When working in the air shot mode a small predetermined air shot dose is pressed out from the ampule when the injection button is actuated. When working in the injection mode, a dose set by operation of the dose setting means is injected by operation of the injection button. The electronic injection device is normally working in the air shot mode but shifts to work in the dose injection mode when it receives a signal indicating that the dose setting means has been operated. The circuit returns to its air shot mode when receiving a signal indicating that the set dose has been injected. This signal can originate either from a switch indicating that the protection cap is mounted or from a switch indicating that the injection button has been pressed.

27 Claims, 3 Drawing Sheets

AIR SHOT MECHANISM FOR ELECTRONIC INJECTION DEVICES

CROSS-REFERENCE TO RELATED APPLICATIONS

This application is a continuation of co-pending application Ser. No. 09/672,662 filed on Sep. 28, 2000, which claims priority under 35 USC 119 of U.S. provisional application Nos. 60/160,130 filed Oct. 18, 1999 and 60/170, 017 filed Dec. 10, 1999 and Danish application nos. PA 1999 01451 filed Oct. 12, 1999 and PA 1999 01732 filed Dec. 3, 1999; the contents of all of the foregoing are hereby incorporated herein by reference in their entireties

BACKGROUND OF THE INVENTION

From U.S. Pat. No. 5,928,201 is known a device by which a dose is set by operating a pair of dose setting buttons, one increasing the set dose step by step and another decreasing the dose step by step when operated. The set dose is stored in a circuit which controls a display to show the set dose and a motor drives a mechanical dose setting device to carefully set a mechanical dose setting device to the dose shown in the display. The injection is performed manually to allow the user to inject the dose with the rate he finds appropriate.

It may be attractive to let the injection be performed electro-mechanically too as then the demand to the users finger strength can be reduced to the force needed to press down an electronic switch button. Further, the mechanical impact on the device is independent on the strength of the user so it is avoided that some users can hardly operate the device whereas others will break it.

Devices wherein the doses are electronically represented also may contain circuitry wherein historical data are stored so it is possible to create a picture of the way the user has followed his treatment, and prospective doses and time intervals can be planned on the basis of the stored data. At least it is appropriate to be able to store the size of the latest injected dose and the time passed since this injection.

In an electronic injection device of the kind described above only a minimum of operation buttons are needed, e.g., a counting up dose set button allowing a stepwise increase of the set dose, a counting down dose set button allowing a stepwise decrease of an erroneously too high set dose, and an injection button by which either the dose is manually injected or the electronic circuit is ordered to energize a motor to inject the set dose.

By injecting medicine from an ampule it is necessary to ensure that no air is left in the ampule when the injection is performed. For this purpose a so-called air-shot is performed. An air shot may be performed by setting a small dose, e.g., one international unit of the medicine to be injected, and make this small dose be pressed out from the ampule holding the device with the needle pointing vertically upward. This procedure can be repeated until it is seen that liquid is sprayed out through the needle where after the dose to be injected can be set, the needle can be inserted into the skin of the user, and an amount of medicine corresponding to the set dose can be pressed out and injected through the needle.

However, this repetitive use of the dose-setting device is not wanted. If the device is provided with a memory which stores historical data for the purpose of controlling the course of a treatment, it is necessary to register which of the doses have been air shot doses and which doses have actually been injected. This problem could be overcome by providing a special air shot button as it is known from syringes by which the injection is performed manually, but this will be on the account of one more button whereby the possibilities for erroneous operation is increased.

An objective of the invention is to provide an injection device by which repetitive air shots can be performed without adding extra operation buttons to the device and without information of the air-shots being stored as a part of the operation history of the device.

SUMMARY OF THE INVENTION

This is obtained by an electronic injection device comprising a housing containing an electronic circuit into which the size of a set dose can be read by operation of dose setting means, an injection button which can be operated to inject a set dose, an ampule from which a medicine can be pressed out through a needle mounted at the distal end of the ampule when the injection button is operated, and a display driven by the electronic circuit to show the dose set by operation of the dose setting means.

It is attractive to set the dose electronically and show the set dose on an electronic display, e.g., an LCD display, as the size of the digits displayed can be made arbitrarily large without being dependent on the distances possible mechanical dose setting parts are moved by the setting of the dose.

The device according to the invention is characterized in that the electronic circuit is designed to work in two alternative modes: an air shot mode in which it controls an automatic pre-setting of a small air shot dose to be pressed out from the ampule when the injection button is actuated, and a dose injection mode in which a dose set by operation of the dose setting means is injected by operation of the injection button, said circuit normally working in the air shot mode but shifting to work in the dose injection mode when it receives a signal indicating that the dose setting means has been operated. The circuit may return to its air shot mode when receiving a signal indicating that a set dose has been injected. This signal may either be a signal from a switch indicating that a protection cap is mounted or a signal from a switch indicating that the injection button has been pressed.

This means that when the device is taken into use but no dose has been set the electronic circuit will work in a mode making it control either a dose setting motor to set a small air shot dose which can be injected by pressing the injection button, or control a motor to press out an air shot dose when the injection button is operated.

The injection button may now be operated one or more times while the device is held with the needle pointing upward until it is seen that liquid and not air is pressed out through the needle.

To ensure that the device is held in the correct position with the needle pointing upward a position indicator may be provided which gives off a signal to the electronic circuit when the device is held in the correct position for an air shot. The signal, which can be an opening or a closing of a switch, can be made a condition that has to be fulfilled before the electric circuit energizes the motor to prepare or perform an air shot. This way waste of medicament, due to the fact that the device is held in a position in which air in the ampule cannot reach the needle, is avoided.

According to the invention the dose setting may be electro-mechanically realized by means of an electric motor which is controlled by the electronic circuit to lift up the injection button from the housing a distance corresponding to the set dose and the injection may be performed manually by pressing home the injection button. The signal that indicates that a set dose has been injected may be a switch that is actuated when the injection button is pressed. The electronic circuit will then prepare a new air shot each time a home pressing of the injection button is performed and the circuit will remain in the air shot mode.

In devices wherein the injection is performed electro-mechanically by a motor controlled by the electronic circuit, actuation of the injection button may make a motor electro-mechanically press out a dose from the ampule, the motor being controlled by the electronic circuit to press out an automatically set small air shot dose when the circuit is working in its air shot mode, and a dose set by operation of the dose setting means when the circuit is working in its dose injection mode.

At the very moment when the dose setting member is operated the working mode of the electronic circuit is changed to an injection mode in which operation of the injection button will result in the injection of a set dose either by directly pressing out a dose corresponding to the distance the injection button has been elevated over the housing by the dose setting motor controlled by the electronic circuit, or by controlling an injection motor to inject the dose set by the operation of the dose setting member, and the circuit will remain in this mode until the injection button has been pressed.

To ensure that at least one air shot is performed in advance of an injection, the circuit may be so designed that it cannot receive a signal from the dose setting means until at least one air shot dose has been administered.

According to the invention the electronic circuit may comprise a memory wherein historical information of injected doses and the time for their injection is stored. As the electronic circuit according to its two working modes can discriminate between air shots and injection of doses set by the user, these historical data can be rid of disturbing air shot data.

The electronic circuit may further be provided with a memory wherein the size of all air shots and injections are summed and subtracted from the size of the total content of a new ampule to leave the memory with an information of the size of the remaining amount of medicine in the ampule.

The set dose currently is compared with the remaining amount of medicine in the ampule to block for setting of a dose exceeding this remaining amount.

DETAILED DESCRIPTION OF THE PRESENTLY PREFERRED EMBODIMENTS

Figure 1:
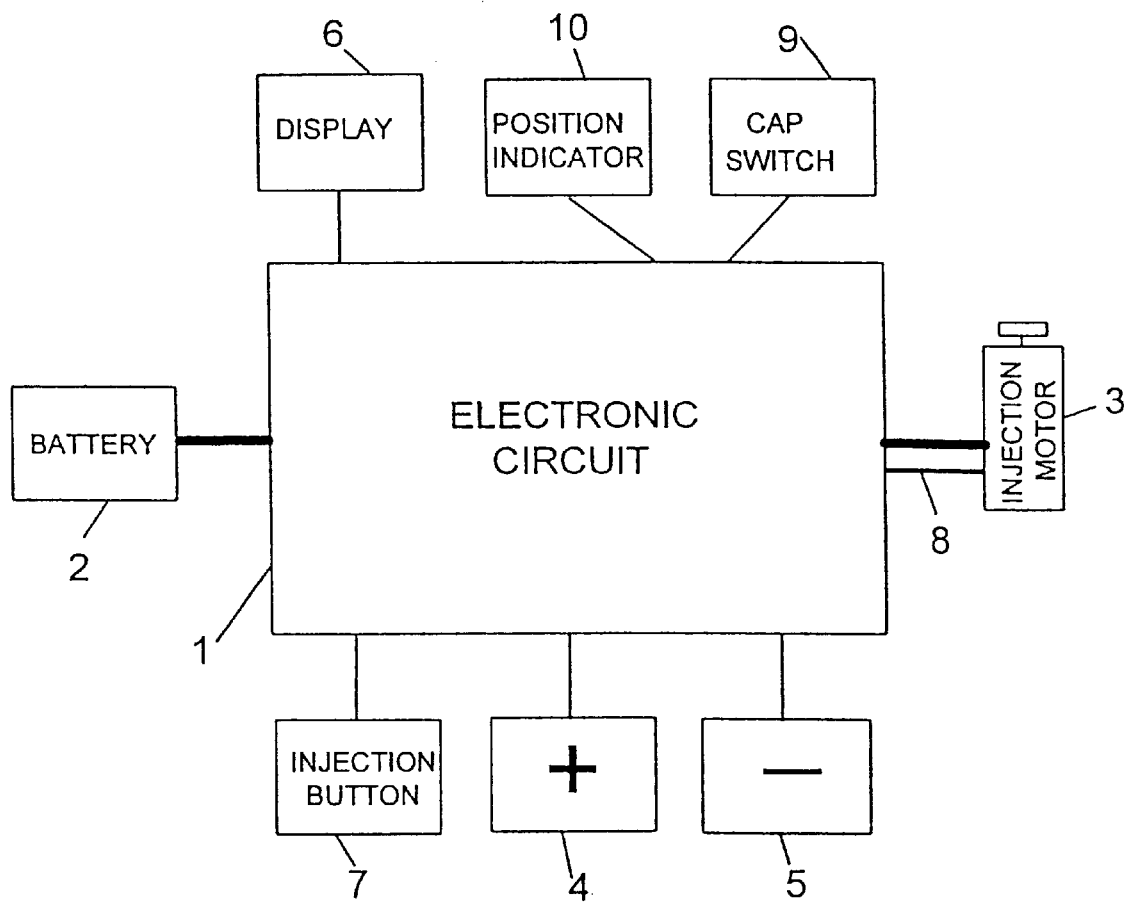
FIG. 1 shows a block diagram of the electronic components of an embodiment of an injection device according to the invention.

In an injection device wherein the dose is injected by means of a motor which when energized presses out medicine from the ampule, an electronic circuit 1 is connected to a battery 2 which supplies the power needed for the operation of the circuit. Further, the battery 2 supplies an injection motor 3 which power supply is controlled by the circuit 1. To the circuit 1 is coupled a set of dose setting buttons 4 and 5, one 4 marked with a "+" and which provides a stepwise increase of the set dose as long as it is pressed, and another 5 marked with a "−" and which provides a stepwise decrease of a set dose as long as it is pressed. During the setting of a dose the size of this set dose can be read on a display 6 coupled to electronic circuit 1. The dose-increasing button 4 is maintained in pressed condition until the display has counted up to the wanted dose, if the wanted dose is exceeded the button 5 is pressed until the display has counted down to the wanted dose. After the dose has been set the set dose is injected by pressing an injection button 7, which makes the circuit energize the motor to drive a mechanical injection mechanism to press out the set dose from the ampule. A data connection 8 from the motor to the electronic circuit provides a feedback to the circuit of the dose injected and when this dose reaches the set dose the energizing of the motor 3 is stopped.

The dose setting is here described as being performed by buttons 4 and 5. Rotating a dose setting wheel or drum whereby a counting up is performed when this wheel is rotated in one direction and a counting down is performed when the wheel is rotated in the opposite direction may alternatively perform the dose setting.

From WO 9733638 it is known to provide a device with a protective cap protecting the needle when the device is not in use. Further a switch is provided which is operated by the cap so that the position of the switch indicates whether the cap is on or not. In the device in FIG. 1 a switch 9 is coupled to the circuit 1 to bring information of the on or off condition of the cap to this circuit. To save battery power consuming parts of the circuit is turned off when the cap is on. This does not apply for possible watch and memory functions which need continuous energizing. When the cap is taken off, a signal is sent to the circuit 1 which is then coupled to work in an air shot mode in which an activation of the injection button 7 will make the circuit energize the motor to make the device administer a pre-set small amount from the ampule, e.g., an amount corresponding to one international unit of the medicine in the ampule. Such an administration will be performed each time the injection button 7 is activated until a dose setting is started. As soon as the circuit receives a signal from the dose setting buttons 4 or 5 indicating that a dose is being set the working mode of the circuit 1 changes to a dose injection mode in which the motor is controlled to administer the set dose when the injection button 7 is pressed. When the set dose has been administered by pressing of the button 7 the circuit will revert to its air shot mode but if a new dose is set after a first dose has been injected the circuit quickly reverts to its dose injection mode until the button 7 is pressed again.

A switch connected to the injection button 7 is actuated each time the injection button is operated. When this switch is actuated it gives off a signal to the circuit, which signal is taken as an indication of the fact that the injection button has been operated.

When the circuit receives this signal it is coupled to work in an air shot mode in which an activation of the injection button 7 will make the circuit energize the motor to make the device administer a pre-set small amount from the ampule, e.g., an amount corresponding to one international unit of the medicine in the ampule. Such an administration will be performed each time the injection button 7 is activated until a dose setting is started. As soon as the circuit receives a signal from the dose setting buttons 4 or 5 indicating that a dose is being set the working mode of the circuit 1 changes to a dose injection mode in which the motor is controlled to administer the set dose when the injection button 7 is pressed. When the button 7 has been pressed to inject the set dose the injection button switch gives off a signal making the circuit change to the air shot mode, but as soon as the dose setting buttons are operated again the circuit will change to the dose injection mode.

During the air shots the device must be held with the needle pointing upward so that possible air in the ampule lies as a bubble adjacent to the needle tip projecting into the ampule. To avoid medicine being wasted due to the fact that the device is not held in the correct vertical position, a direction indicator 10 may be included in the device, which indicator provides a signal that informs the circuit whether the position of the device is appropriate for an air shot. The signal can control the circuit to only energize the motor to perform an air shot when the device is in the correct position for such an air shot. When the circuit works in its dose-injecting mode the position will have no influence on the energizing of the motor 3.

Figure 2:
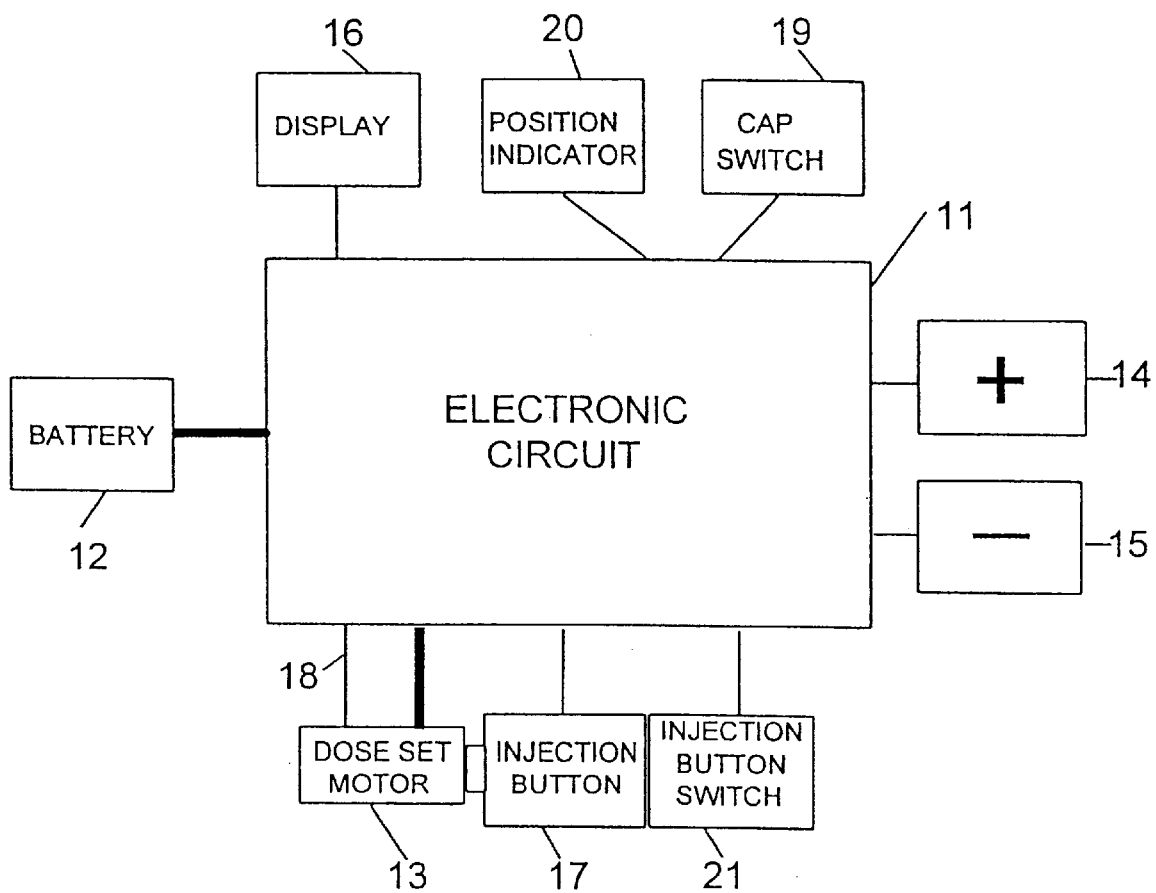
FIG. 2 shows a block diagram of the electronic components of another embodiment of an injection device according to the invention.

In a syringe according to FIG. 2, wherein an injection button 17 is elevated over the housing of the device a distance corresponding to a set dose by means of a motor 13, the power necessary for the running of the device is delivered by a battery 12 which energizes an electronic circuit 11 which functions much like the circuit 1 in FIG. 1. A dose is set by the dose setting buttons 14 and 15 that control a counting up and down of a set dose size in the circuit 11. The set dose is shown in a display 16 and the motor 13 performs a mechanical setting of the dose by elevating the injection button 17 a distance corresponding to the set dose as the circuit controls the motor 13 to make it perform the elevation needed. A feedback 18 from the motor to the circuit enables this circuit to decide when the injection button has been elevated a distance corresponding to the dose read into the circuit by the operation of the dose setting buttons 14 and 15.

In the device described in FIG. 2 the air shot is obtained by the fact that the motor automatically elevates the injection button 17 a distance corresponding to an air shot dose as long as the circuit works in its air shot mode what it does after each pressing of the injection button 17. When one of the dose setting buttons 14 or 15 is operated the circuit 11 shifts to a dose injection mode and controls the motor 13 to elevate the injection button 17 a distance corresponding to the set dose. When the injection button is pressed the set dose is injected and the injection button sends a signal to the circuit 11 to make this circuit revert to the air-shot mode.

The device according to FIG. 2 is further provided with a position indicator 20 which gives off a signal to the electronic circuit which will only allow setting of an air shot dose when the device is held in a position vertical position with the needle pointing upward. The air shot function may be repeated as long as the dose setting buttons 14 or 15 are not operated. The actuation of the injection button 21 switch sends a signal to the electronic circuit making this circuit attain the air shot mode in which it controls the injection button to be elevated again after an air shot until a signal from one of the dose setting buttons 14 or 15 makes the electronic circuit shift to its dose injection mode.

Figure 3:
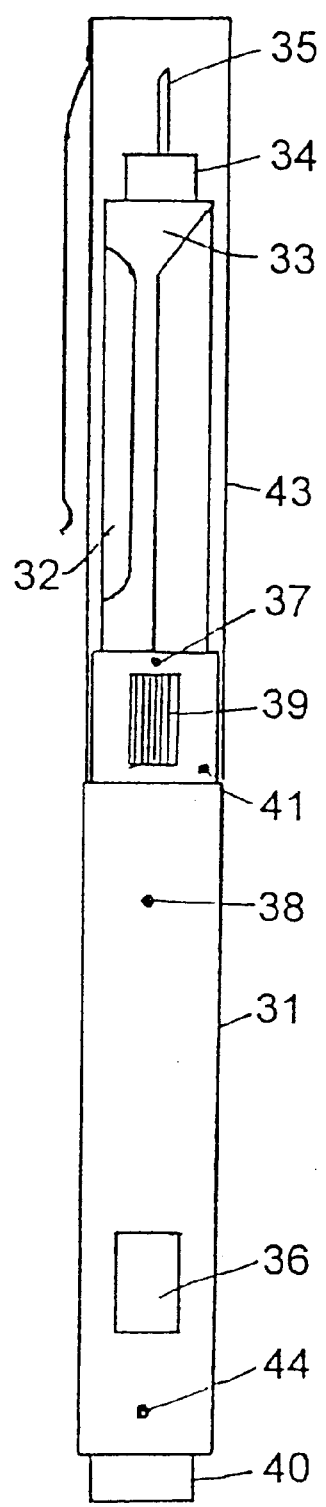
FIG. 3 schematically shows an injection device according to the invention.

FIG. 3 shows schematically an injection device comprising a housing 31 in which an ampule holder 33 holds an ampule 32. A needle hub 34 with an injection needle 35 is mounted at the distal end of the ampule so that a not shown rear needle is penetrating the sealing of the ampule. A dose-setting wheel 39 can be rotated in one direction to count up a dose or in the opposite direction to count down a too large set dose. Turning of the dose setting wheel 39 is by a signal generator or switch 37 reported to a not shown electronic circuit in the housing and the set dose is shown in a display 36. An injection button 40 is provided the operation of which will result in administration of a dose, which dose depending on the operation mode of the electronic circuit is a fixed small air shot dose or the dose shown in the display 36.

When a cap 43 protecting the needle 35 is removed and a switch 41 reports to the electronic circuit that the device is going to be taken into use, the electric interfaces that have been shut off during the storing of the device are energized.

Depending on the embodiment of the injection device the injection button 40 can operate an electric switch that activates the electronic circuit to energize a motor, which moves a piston into the ampule to press out some of the content of this ampule through the needle 35. In another embodiment of the injection device the button is mechanically lifted up from the end of the housing 31 a distance corresponding to the size of a set dose. In this embodiment the button is automatically elevated a distance corresponding to an air shot when the cap 43 is removed and an air shot is administered by pressing the button 40 home. As it may be necessary to repeat the air shot procedure, a switch 44 is provided which reports to the electronic circuit that the button 40 has been pressed home. As the circuit attains its air shot mode when it receives this signal, the button is again automatically elevated to a position corresponding to an air shot whereas it is elevated a distance corresponding to the dose set by the dose setting wheel 39 when this wheel is operated and the circuit is shifted to its injection mode.

The dose setting device is described as a dose setting wheel but it may as well be a count up button and a count down button without departing from the scope of the invention.

What is claimed is:

1. An electronic injection device, comprising:
    a housing containing an electronic circuit into which the size of a set dose can be read by operation of dose setting means,
    an injection button which can be operated to inject a set dose,
    an ampoule from which the set of medicine can be pressed out through a needle mounted at the distal end of the ampoule by an electrical driven motor when the injection button is operated, and
    an air-shot means that when actuated causes an air-shot signal to be sent to the electronic circuit, the electronic circuit actuating the motor to expel a pre-set, non adjustable small air shot dose from the cartridge.

2. The electronic injection device of claim 1, wherein the electronic circuit comprises a display driven by the electronic circuit to show the dose set by operation of the dose setting means.

3. The electronic injection device of claim 1, wherein the injection device further is provided with a cap switch which cap switch is coupled to the electronic circuit to bring information of the on or off condition of the cap switch.

4. The electronic injection device of claim 1, wherein a position indicator is provided which controls the electronic circuit to only perform the administration of an air-shot dose when the position indicator indicates that the device is held vertically with the needle pointing upward.

5. The electronic injection device of claims 1, 2, 3 or 4; wherein the electronic circuit comprises a memory wherein historical information of doses are stored and which memory can discriminate between expelling of set doses and air-shot doses.

6. The electronic injection device of claim 5, wherein the size of all air shot doses and injection doses are summed in the memory and subtracted from the size of the total content of a new ampoule to leave the memory with an information of the size of the remaining amount of medicine in the ampoule.

7. The electronic injection device of claim 6, wherein the set dose is compared with the remaining amount of medicine in the ampoule.

8. An injection device comprising:
   a cartridge of medicament;
   a drive mechanism configured to expel medicament from the cartridge;
   an electronic control unit that actuates the drive mechanism;
   a means for setting a desired dose to be expelled from the cartridge; and
   wherein the control mechanism is configured so that at the request of a user the drive mechanism is actuated to expel an a predetermined air shot dose from the cartridge, without the need for the user to select the size of the air shot dose.

9. The device of claim 8, further comprising a button that is electronically connected to the electronic control unit, the button being activate able byte user and upon activation by the user capable of sending the request for the air shot dose to the electronic control unit.

10. The device of claim 8, further comprising an orientation sensor means for sending a signal to the electronic control unit that the device is oriented in a predetermined manner and wherein the air shot dose is expelled only when the device is in the predetermined orientation.

11. The device of claim 9, further comprising an orientation sensor means for sending a signal to the electronic control unit that the device is oriented in a predetermined manner and wherein the air shot dose is expelled only when the device is in the predetermined orientation.

12. The device of claim 10 wherein the processor is configured to keep track of the total volume of medicament in the cartridge originally and to track the used volume from both user set doses and air shot doses, thereby tracking the remaining medicament in the cartridge.

13. A method for priming and injecting a dose of medication from an electronic injection device having an electronic control unit and a drive mechanism for expelling medicament contained within the device, the method comprising:
   a. pressing a button to send a signal to an electronic control mechanism to prime the device by expelling a predetermined air-shot dose;
   b. actuating the drive mechanism, upon receipt of the signal from step a, to expel a predetermined air shot dose from the cartridge, wherein the size of the dose is automatically, without user intervention, determined by the electronic control unit;
   c. setting a predetermined dose of medication to inject;
   d. injecting the predetermined dose of medication; and
   wherein steps a and b may be performed before or after step c but wherein steps a–c are performed prior to step d; and
   wherein the method of steps a–d are repeated.

14. The method of claim 13, further comprises checking whether the device is in a predetermined orientation prior to step b.

15. The method of claim 13, further comprising tracking the volume of medication remaining in the cartridge by substracting each air shot dose and each user selected dose from the original volume of medication.

16. A medication delivery device comprising:
   a. a cartridge containing a medication;
   b. an electronic control unit;
   c. a plurality of buttons connected to the electronic control unit so that a user may interface with the electronic control unit;
   d. a motorized drive mechanism for expelling medication from the cartridge;
   e. wherein the electronic control unit is configured to accept a dose size from the user and to control the motorized drive mechanism to expel the dose from the cartridge upon receipt of a dosing instruction from the user; and
   f. wherein the controller is configured to prime the device prior to injecting the user selected dose, by receiving a command from the user, wherein the command is sent to the control by the user pressing one of the buttons, and wherein the priming occurs by expelling a pro-selected non-user settable air shot dose.

17. The device of claim 16, wherein the controller is configured to prime the device only when the device is in a predetermined orientation.

18. An electronic injection device, comprising:
   a housing containing an electronic circuit into which the size of a set dose can be inputted by operation of dose setting means,
   an injection button that can be operated to inject a set dose,
   an ampoule from which the set of medicine can be pressed out through a needle mounted at the distal end of the ampoule by an electrical driven motor when the injection button is operated,
   further comprising a means for driving out a pre-set small air-shot dose from the cartridge with the aid of the motor upon receipt of an air-shot signal from said circuit.

19. The electronic injection device of claim 18, wherein the electronic circuit comprises a display driven by the electronic circuit to show the dose set by operation of the dose setting means.

20. The electronic injection device of claim 18, wherein the injection device further is provided with a cap switch which cap switch is coupled to the electronic circuit to bring information of the on or off condition of the cap switch.

21. The electronic injection device of claim 18, wherein a position indicator is provided which controls the electronic control to only perform the administration of an air-shot dose when the position indicator indicates that the device is held vertically with the needle pointing upward.

22. The electronic injection device of claim 18, 19, 20 or 21, wherein the electronic control comprises a memory wherein historical information of doses are stored and which memory can discriminate between expelling of set doses and air-shot doses.

23. The electronic injection device of claim 22, wherein the size of all air shot doses and injection doses are summed in the memory and subtracted from the size of the total content of a new ampoule to leave the memory with an information of the size of the remaining amount of medicine in the ampoule.

24. The electronic injection device of claim 23, wherein the set dose is compared with the remaining amount of medicine in the ampoule.

25. A method of performing an air-shot in an electronic injection device comprising an electrical motor wherein the method comprises the step of energizing the motor such that the motor drives a mechanical injection mechanism forward to press out a pre-set, non-adjustable air-shot dose from the cartridge.

26. An electronically controlled motorized injection device comprising:

a motorized drive means for expelling medication from the device;

a first circuit for inputting a user selected dose size to be expelled;

a second circuit for priming the device to expel a small predetermined non-adjustable air shot dose;

a third circuit for driving the motorized drive means to expel either the air shot dose or the user selected dose.

27. The device of claim 26, further comprising a fourth circuit for determining whether the device is oriented in a predetermined position and wherein the fourth circuit prevents priming of the device unless the device is oriented in the predetermined position.

* * * * *

UNITED STATES PATENT AND TRADEMARK OFFICE
CERTIFICATE OF CORRECTION

PATENT NO.        : 6,726,661 B2
APPLICATION NO. : 10/315871
DATED             : April 27, 2004
INVENTOR(S)       : Munk et al.

It is certified that error appears in the above-identified patent and that said Letters Patent is hereby corrected as shown below:

Claim 9

Column 7, Line 25

Change "byte" to --by the-- before "user"

Claim 16

Column 8, Line 21

Change "pro-selected" to --pre-selected--

Signed and Sealed this

Twenty-first Day of August, 2007

JON W. DUDAS
*Director of the United States Patent and Trademark Office*